United States Patent
Liu et al.

(10) Patent No.: US 10,640,728 B2
(45) Date of Patent: May 5, 2020

(54) METHOD FOR PREPARING RAPESEED OIL BY SEMI-SOLID AQUEOUS ENZYMATIC TREATMENT

(71) Applicants: Yuanfa Liu, Wuxi (CN); Peirang Cao, Wuxi (CN); Jinwei Li, Wuxi (CN); Liang Zhang, Wuxi (CN)

(72) Inventors: Yuanfa Liu, Wuxi (CN); Peirang Cao, Wuxi (CN); Jinwei Li, Wuxi (CN); Liang Zhang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 25 days.

(21) Appl. No.: 15/980,218

(22) Filed: May 15, 2018

(65) Prior Publication Data

US 2018/0258369 A1    Sep. 13, 2018

Related U.S. Application Data (63) Continuation of application No. PCT/CN2015/096664, filed on Dec. 8, 2015.

(30) Foreign Application Priority Data

Nov. 25, 2015    (CN) .......................... 2015 1 0831700

(51) Int. Cl.
| | |
|---|---|
| *A61K 36/31* | (2006.01) |
| *C11B 1/02* | (2006.01) |
| *A23D 9/04* | (2006.01) |
| *A23K 20/158* | (2016.01) |
| *A23K 50/50* | (2016.01) |
| *A23L 33/115* | (2016.01) |
| *C11B 1/04* | (2006.01) |
| *C11B 1/06* | (2006.01) |

(52) U.S. Cl.
CPC ............... *C11B 1/025* (2013.01); *A23D 9/04* (2013.01); *A23K 20/158* (2016.05); *A23K 50/50* (2016.05); *A23L 33/115* (2016.08); *A61K 36/31* (2013.01); *C11B 1/04* (2013.01); *C11B 1/06* (2013.01); *C12Y 302/01004* (2013.01); *C12Y 302/01015* (2013.01); *C12Y 304/25001* (2013.01); *A23V 2002/00* (2013.01); *A61K 2236/00* (2013.01)

(58) Field of Classification Search
None
See application file for complete search history.

(56) References Cited

U.S. PATENT DOCUMENTS

| | | | | |
|---|---|---|---|---|
| 9,034,612 | B2 * | 5/2015 | Lam ..................... | C12P 7/6418 435/134 |
| 9,243,267 | B2 * | 1/2016 | Lam ..................... | C12P 7/6418 |
| 2008/0305531 | A1 * | 12/2008 | Lam ..................... | C12P 7/6418 435/142 |
| 2016/0168604 | A1 * | 6/2016 | Lam ..................... | C12P 7/6418 435/134 |

FOREIGN PATENT DOCUMENTS

CN    102796612 A    11/2012

OTHER PUBLICATIONS

Rosenthal, A. et al. Aqueous and Enzymatic Processes for Edible Oil Extraction. Enzyme and Microbial Technology 19:402-420, 1996. (Year: 1996).*
Ohlson, R. Modern Processing of Rapeseed. JAOCS 69(3)195-198, Mar. 1992. (Year: 1992).*
Dominguez H. et al. Enzymatic Pretreatment to Enhance Oil Extraction from Fruits and Oilseeds: A Review. Food Chemistry 49(3)271-286, 1994. (Year: 1994).*

* cited by examiner

Primary Examiner — Ralph J Gitomer
(74) Attorney, Agent, or Firm — Lili Chen (57) ABSTRACT

The invention discloses a method for preparing rapeseed oil by a semi-solid aqueous enzymatic process, belonging to the field of functional foods and health care products. The present invention first prepares a semi-solid rapeseed paste with 3.5-4.5% moisture content, which is hydrolyzed by a mixture of pectinase, cellulase and alkaline protease to extract rapeseed oil. The resulting rapeseed oil contains high levels of active ingredients including totaxin, sterol, phenols and beta-carotene. The rapeseed oil of the invention can be added into animal feeds, which helps to reduce animal blood lipid levels and body weight. It can significantly reduce the contents of total triglyceride, total cholesterol and LDC-C in the blood, and, at the same time, increases the level of HDL-C in the blood. In addition, the rapeseed oil prepared by the present invention can relieve hepatic steatosis in hyperlipemia rats.

7 Claims, 7 Drawing Sheets

METHOD FOR PREPARING RAPESEED OIL BY SEMI-SOLID AQUEOUS ENZYMATIC TREATMENT

CROSS-REFERENCES AND RELATED APPLICATIONS

This application is a continuation of the international application PCT/CN2015/096664, with an international filing date of Dec. 8, 2015, which claims priority to Chinese application CN201510831700.X, filed Nov. 25, 2015, the contents of which are herein incorporated by reference in its entirety.

BACKGROUND OF THE INVENTION

Field of the Invention

The disclosure herein relates to a method for preparing rapeseed oil by semi-solid aqueous enzymatic treatment, which belongs to the field of functional foods and health care products.

Description of the Related Art

Rapeseed oil is one of the four major vegetable oils in the world, and its annual production is only second to that of palm oil and soybean oil. Rapeseed oil is extracted from the seeds of canola, which is typically a yellow or amber liquid and contains a relatively high amount of oleic and linoleic acids.

With large reserves and many different varieties, rapeseed oil becomes a main vegetable oil in China. The quality of rapeseed oil is closely related to the health of the people in China. With the development of the oil industry, the composition of oils and fats in vegetable oils, such as unsaturated fatty acids and the biologically active ingredients that have special physiological effects on the human body, have gradually gained attention. In particular, trace components, although low in content, are associated with certain nutrition and health benefits of oils and fats. Therefore, while the current researchers are developing high-yield crops, they are, at the same time, moving toward the development of oil products with special nutritional and functional ingredients. For example, phytosterols have structural characteristics similar to cholesterol and are able to compete with cholesterol molecules in the intestine to form chylomicrons, and its co-crystallization with cholesterol can increase the excretion of cholesterol. Lipid-enriched VE is capable of inhibiting low density lipoprotein (LDL) oxidation through its unique affinity with lipoprotein, which can be used in the prevention of cardiovascular and cerebrovascular diseases. Plant polyphenols in oils and fats can also effectively reduce the risk of cardiovascular disease.

The contents of trace active ingredients such as tocopherols, sterols, phenols, and beta-carotene, which are rich in rapeseed oil, can affect the quality of the oil product. There are currently four types of methods for producing rapeseed oil. The cold pressing method is to obtain rapeseed oil by pressing rapeseeds at less than 60° C.; the hot pressing method is to obtain the oil by steaming and frying rapeseeds at 120° C.; and the leaching method is to extract rapeseed oil with an organic solvent such as n-hexane. Aqueous enzymatic hydrolysis method uses proteases to hydrolyze oil bodies and separates proteins and oils by centrifugation. Among these four methods, rapeseed oil prepared by aqueous enzymatic method has the best quality. Because of its mild preparation conditions, the trace active ingredients such as tocopherols, phenols, beta-carotene are better retained. In the traditional process of aqueous enzymatic preparation of rapeseed oil, rapeseeds and water are mixed at a ratio of 1:4-6 (wt/wt), and an enzyme mixture is added to the rapeseed-water mixture and the hydrolysis reaction is carried out in a liquid state. The traditional method has serious shortcomings, such as low yield and emulsification problem. It requires a further demulsification treatment, which causes a waste of energy and time. At the same time, due to the high water content in traditional water enzymatic methods, high polarity molecules such as phenolic substances are easily dissolved in water, leading to the loss of such trace nutrients.

DETAILED DESCRIPTION

The present invention provides a method for producing rapeseed oil by a semi-solid aqueous enzymatic process, comprising the following steps:

(1) rapeseeds are cleaned to remove the debris, shriveled seeds, and impurities;

(2) the moisture content of the rapeseeds is adjusted to 8-10 wt %;

(3) the rapeseeds obtained in the previous step are pressed to obtain rapeseed embryo flakes which are treated at 50° C.-70° C. to adjust the moisture content to 3.5-4.5 wt %, and mature rapeseed flakes are thus obtained;

(4) the mature rapeseed flakes are crushed and sieved to obtain an oil-producing powder; the oil-producing powder and water are mixed at a mass ratio of 1:1 to make a semi-solid rapeseed paste; 0.5% to 2% (w/w) of the total enzyme (pectinase:cellulase:alkaline protease=1:1:1, by weight) is added to the semi-solid rapeseed paste, stirring and mixing at 40-60° C. for 1-2 hr; the rapeseed paste is then centrifuged to separate crude oil from solid residues; finally, water is added to the crude oil at 0.2-0.4 L/kg oil, and the oil-water mixture is centrifuged at 40-60° C. to obtain the clear rapeseed oil, which is further dried under vacuum to obtain the final rapeseed oil product.

In one embodiment of the present invention, enzyme treatment temperature of step (4) is under gradient temperature control by following steps: keep the temperature at 40° C. for 20-40 min, raise the temperature to 60° C. within 20-40 min, and then maintain it at 60° C. for 20-40 min. The enzyme efficiency is significantly improved under the gradient temperature control, leading to an increase of the oil yield.

In one embodiment of the present invention, the mature rapeseed flakes are crushed and sieved through a 40~80 mesh sieve.

In one embodiment of the present invention, the mixing step is carried out under 10~20 rpm at 20-40° C.

In one embodiment of the present invention, the separation of the crude oil and the solid residues is carried out by centrifugation at 3500 rpm.

In one embodiment of the present invention, the clear rapeseed oil is obtained by centrifugation at 6500 rpm.

In one embodiment of the present invention, the enzyme activity of pectinases, cellulases and alkaline protease is 1.5 AU/g, 2.4 AU/g and 1.5 AU/g. respectively. The AU stands for anson unit.

In one embodiment of the present invention, the step (4) comprises the following steps: the mature rapeseed flakes are crushed and sieved through a 40-80 mesh sieve to obtain an oil-producing powder; the oil-producing powder and water are mixed at a mass ratio of 1:1 to make a semi-solid rapeseed paste; 0.5% to 2% (w/w) of the total enzyme (pectinase:cellulase:alkaline protease=1:1:1, by weight) is added to the rapeseed paste, stirring and mixing at 10-20 rpm, 40-60° C. for 1-2 hr; the rapeseed paste is then centrifuged at 3500 rpm to separate crude oil from solid residues; finally, water is added to the crude oil at 0.2-0.4 L/kg oil, and the oil-water mixture is centrifuged at 6500 rpm, 40° C. to obtain the clear rapeseed oil, which is further dried under vacuum to obtain the final rapeseed oil product.

The present invention also provides application methods of the rapeseed oil prepared by the above methods.

In one embodiment of the present invention, the rapeseed oil is added into animal feeds.

In one embodiment of the present invention, the feeds with the rapeseed oil comprises 1% cholesterol, 0.2% sodium cholate, 10% lard oil, 10% rapeseed oil, 10% dried egg yolks, and 68.85% basic feed.

The present invention has the following benefit:

(1) The present invention employs a simple semi-solid water enzymatic method to prepare rapeseed oil, using the pectinase, cellulase and alkaline protease to carry out enzymolysis. Combined with gradient temperature control strategy, the yield of clear oil can reach up to 93.5%.

(2) The present invention employs a simple process and mild conditions, which does not require the use of organic solvents, and is safe and non-toxic. The rapeseed oil obtained by this method has high quality and retains more trace active ingredients than those made by other methods. The content of tocopherols, sterols, phenols, β-carotene can reach 672 ppm, 5869 ppm, 154 ppm, and 5.8 ppm, respectively, which is significantly higher than those made by the traditional aqueous enzymatic and low-water enzymatic methods.

(3) The rapeseed oil of the present invention, when used in animal feeds, can significantly suppress the increase of body weight in hyperlipidemia rats, reduce the accumulation of fat, and significantly reduce total triglyceride (TG) and total cholesterol (TC) in serum, and increase serum high density lipoprotein cholesterol (HDL-C) content. The rapeseed oil prepared by this method can improve hepatic steatosis in hyperlipidemic rats.

(4) The rapeseed oil of the present invention can be used in drugs or foods for preventing, relieving, or treating the diseases or physical discomforts related to elevated blood lipids. The hyperlipidemia described therein refers to hypercholesterolemia, hypertriglyceridemia, mixed hyperlipidemia, or low-density lipoproteinemia. The diseases or physical discomforts associated with elevated blood lipids described therein include is atherosclerosis, coronary heart disease, stroke or myocardial infarction.

EXAMPLES

Example 1: Preparation of Rapeseed Oil by a Semi-Solid Aqueous Enzymatic Method

The preparation process was as follows:

(1) rapeseeds were cleaned to remove the debris, shriveled seeds, and impurities;

(2) the moisture content of the rapeseeds was adjusted to 8 wt %;

(3) the rapeseeds obtained in the previous step were pressed to obtain rapeseed embryo flakes which were treated at 50° C.-70° C. to adjust the moisture content to 4.5 wt %, and mature rapeseed flakes were thus obtained;

(4) the mature rapeseed flakes were crushed and sieved through a 40 mesh sieve to obtain an oil-producing powder; the oil-producing powder and water were mixed at a mass ratio of 1:1 to make a semi-solid rapeseed paste; 0.5% (w/w) of the total enzyme (pectinase (Novozymes, Copenhagen, Denmark):cellulase (Novozymes, Copenhagen, Denmark): alkaline protease (Novozymes, Copenhagen, Denmark)=1: 1:1, by weight) was added to the semi-solid rapeseed paste, and the mixture was stirred at 10 rpm, keeping the temperature at 40° C. for the first 40 minutes, raising the temperature to 60° C. within 40 minutes, and maintaining at 60° C. for another 40 minutes; the rapeseed paste was then centrifuged at 3500 rpm to separate crude oil from solid residues; finally, water was added to the crude oil at 0.2 L/kg oil, and the oil-water mixture was centrifuged at 6500 rpm, 40-60° C. to obtain the clear rapeseed oil, which was further dried under vacuum to obtain the final rapeseed oil product. No further refinement is needed.

Example 2: Preparation of Rapeseed Oil by a Second Semi-Solid Aqueous Enzymatic Method The preparation process was as follows:

(1) rapeseeds were cleaned to remove the debris, shriveled seeds, and impurities;

(2) the moisture content of the rapeseeds was adjusted to 10 wt %;

(3) the rapeseeds obtained in the previous step were pressed to obtain rapeseed embryo flakes which were treated at 50° C.-70° C. to adjust the moisture content to be 3.5 wt %, and mature rapeseed flakes were thus obtained;

(4) the mature rapeseed flakes were crushed and sieved through a 80 mesh sieve to obtain an oil-producing powder; the oil-producing powder and water were mixed at a mass ratio of 1:1 to make a semi-solid rapeseed paste; 2% (w/w) of the total enzyme (pectinase:cellulase:alkaline protease=1: 1:1, by weight) was added to the rapeseed paste, and the mixture was stirred at 10 rpm, keeping the temperature at 40° C. for the first 40 minutes, raising the temperature to 60° C. within 40 minutes, and maintaining at 60° C. for another 40 minutes; the rapeseed paste was then centrifuged at 3500 rpm to separate crude oil from solid residues; finally, water was added to the crude oil at 0.4 L/kg oil, and the oil-water mixture was centrifuged at 6500 rpm, 40-60° C. to obtain the clear rapeseed oil, which was further dried under vacuum to obtain the final rapeseed oil product. No further refinement is needed.

Example 3: Comparison of Rapeseed Oil Produced by Conventional, Low-Moisture Content, and Semi-Solid Aqueous Enzymatic Methods The rapeseed oil was produced by conventional, low-moisture and semi-solid (Example 1~2) aqueous enzymatic methods, respectively. The content of tocopherol, sterol, phenols and β-carotene in the resulting oil product were determined and the results were shown in Table 1.

The conventional aqueous enzymatic method: rapeseeds were crushed and water was added to the crushed rapeseeds at a mass ratio of 1:4~6 (rapeseeds:water), and then pectinase, cellulases, proteases were added. The enzymatic hydrolysis was performed in the aqueous phase, leaching liquid fat and oil from solid oil particles. Due to the high water content, the emulsion was easily formed between the oil and the protein solution, leading to a low yield of clear oil of only about 50%, and making it difficult for the subsequent separation and extraction.

The low-moisture aqueous enzymatic method: the pre-processing of rapeseeds was performed under a solid to liquid ratio of 1:0.1~0.4 (w:w), and the organic solvent was used to leach the oil and fat. The oil extraction rate (the extracted oil (the sum of clear oil and emulsified oil)/the total oil in the rapeseeds) was improved by this method as compared to the conventional method, but the residual organic solvent in the oil product can be a health concern for consumers.

TABLE 1

Comparison of the trace components in rapeseed oil that are prepared by different methods

| trace components (ppm) | conventional water enzymatic: | low moisture water enzymatic | the present invention |
|---|---|---|---|
| tocopherol | 498~524 | 567~602 | 672~700 |
| sterol | 4652~4872 | 4958~5230 | 5869~6000 |
| phenols | 59~67 | 78~129 | 154~170 |
| β-carotene | 2.8~3.5 | 4.1~5.9 | 5.8~6.4 |

As shown in Table 1, the content of tocopherol, sterol, phenols and β-carotene in the rapeseed oil prepared by the present invention were significantly higher than those of other methods.

Example 4. The Effects of the Extraction Process on the Yield of Rapeseed Oil The method of Example 1 was used to prepare rapeseed oil, wherein only the ratio of oil and water in the extraction step (4) was varied. The results are shown in Table 2. The results show that using the 1:1 (crude oil:water, kg/L) extraction solution can significantly increase the clear oil yield. The clear oil yield is defined as the percentage of the clear oil mass in total oil mass of the rapeseeds.

TABLE 2

Comparison of clear oil yields using different extraction solutions

| oil to water ratio in the extraction solution (kg/L) | Yield of clear oil |
|---|---|
| 1:0.1 | 85.6% |
| 1:0.2 | 82.1% |
| 1:0.5 | 89% |
| 1:1 | 93.5% |
| 1:2 | 79% |
| 1:5 | 51% |

The yield of clear oil=mass of clear oil/mass of total oil in rapeseed flakes (%).

Example 5. Effects of Different Rapeseed Oil Products on Hyperlipidemia Rat

Male rats (170±10 g) were fed under the same condition for 7 days, 56 of which were randomly divided into 7 groups named Group A~G, which were respectively fed under following conditions.

The Group A was set as control and the rats in Group A were given normal feeds. The rats in Group B were given high fat feeds containing: 68.85% normal feeds, 1% cholesterol. 0.2% sodium cholate, 20% lard, 10% egg yolk; the other 5 groups were given high fat feeds according to Group B where 10% lard was replaced with 10% rapeseed oils that were produced from different methods. The rapeseed oil was produced by refined, cold-pressed, hot-pressed and semi-solid aqueous enzymolysis (of the present invention) and solvent extraction methods, which were used in Group C, D, E, F, and G, respectively.

After 12 weeks of feeding with normal or high-fat diets, the rats in Group A-G were weighed after fasting for 12 hours. After animals being anaesthetized by chloral hydrated, the heart was punctured and the blood was collected. The supernatant of the blood was obtained by centrifugation. Biochemical indexes such as cholesterol (TC), plasma triacylglycerol (TG), high-density lipoprotein cholesterol (HDL-C), and low-density lipoprotein cholesterol (LDL-C) in serum were measured using a medical kit. The liver tissue (approximately 1 cm×1 cm in size) was placed in a 4% paraformaldehyde fixing solution for tissue fixation, and paraffin sections and H/E tissue staining were performed to observe the morphology of the liver tissue.

(1) Effects of Feeding Hyperlipidemia Rat with Rapeseed Oils on their Body Weight and Body Fat Percentage As shown in Table 3, feeding rats with the rapeseed oil of the present invention can inhibit the increase of body weight and body fat percentage in hyperlipidemia rats.

TABLE 3

Effects of feeding rapeseed oils on body weight and liver weight of hyperlipidemia rats (mean ± SD, n = 8)

| Group | weight (g) | Liver weight (g) |
|---|---|---|
| A | 611.1 ± 29.2 | 16.83 ± 1.18 |
| B | 675.6 ± 38.3 | 31.54 ± 5.06 |
| C | 678.7 ± 74.1 | 33.95 ± 5.02 |
| D | 670.5 ± 37.7 | 31.33 ± 3.59 |
| E | 697.4 ± 85.9 | 33.81 ± 6.21 |
| F | 650.1 ± 48.6 | 29.77 ± 3.88 |
| G | 711.7 ± 57.3 | 34.59 ± 5.89 |

(2) Effects of Feeding Hyperlipidemia Rats with Rapeseed Oils on their Blood Biochemical Indicators As shown in Table 4, the TG and the TC level of the rats from Group F (rapeseed oil of the invention) were lower than those from Groups B, C, E and G. Compared with Group B, the TG and the TC level of the rats from Group F reduced 28% and 12%, respectively.

TABLE 4

Effects of feeding hyperlipidemia rats with rapeseed oils on their blood TCH, TG levels (mean ± SD, n = 8)

| Group | TC (mg/dL) | TG (mg/dL) |
|---|---|---|
| A | 51.34 ± 12.49 | 58.51 ± 18.54 |
| B | 99.69 ± 10.82 | 75.64 ± 19.08 |
| C | 86.77 ± 14.53 | 88.35 ± 19.72 |
| D | 85.19 ± 12.86 | 66.88 ± 11.39 |
| E | 91.17 ± 12.28 | 87.68 ± 18.42 |
| F | 72.68 ± 15.79 | 66.71 ± 16.62 |
| G | 98.16 ± 12.11 | 74.81 ± 19.00 |

TABLE 5

Effects of feeding hyperlipidemia rats with rapeseed oils on their LDL-C, HDL-C levels (mean ± SD, n = 8)

| Group | LDL-C (mg/dL) | HDL-C (mg/dL) |
|---|---|---|
| A | 13.74 ± 1.43 | 54.90 ± 5.09 |
| B | 55.17 ± 5.58 | 48.57 ± 4.82 |
| C | 48.19 ± 4.82 | 43.52 ± 4.38 |
| D | 53.86 ± 5.43 | 33.31 ± 3.32 |
| E | 56.98 ± 5.75 | 47.78 ± 4.71 |
| F | 35.02 ± 3.54 | 46.97 ± 4.70 |
| G | 72.04 ± 7.25 | 24.34 ± 2.40 |

When the body LDL-C (commonly known as bad cholesterol) content is too high, it can deposit on the walls of the heart and brain blood vessels, leading to atherosclerosis. Table 5 shows that the LDL-C in the high-fat diet Group B was increased by 300% compared with that of the normal control Group A ($P<0.05$). The blood LDL-C level of rats fed with rapeseed oil of the invention (Group F) was lowest among the high fat diet groups, which is 36% lower than that in Group B. There was no significant difference in the HDL-C levels between Group B and F. Among all the high fat diet groups, the LDL-C level was the highest and the HDL-C level was the lowest in Group G.

Figure 1:
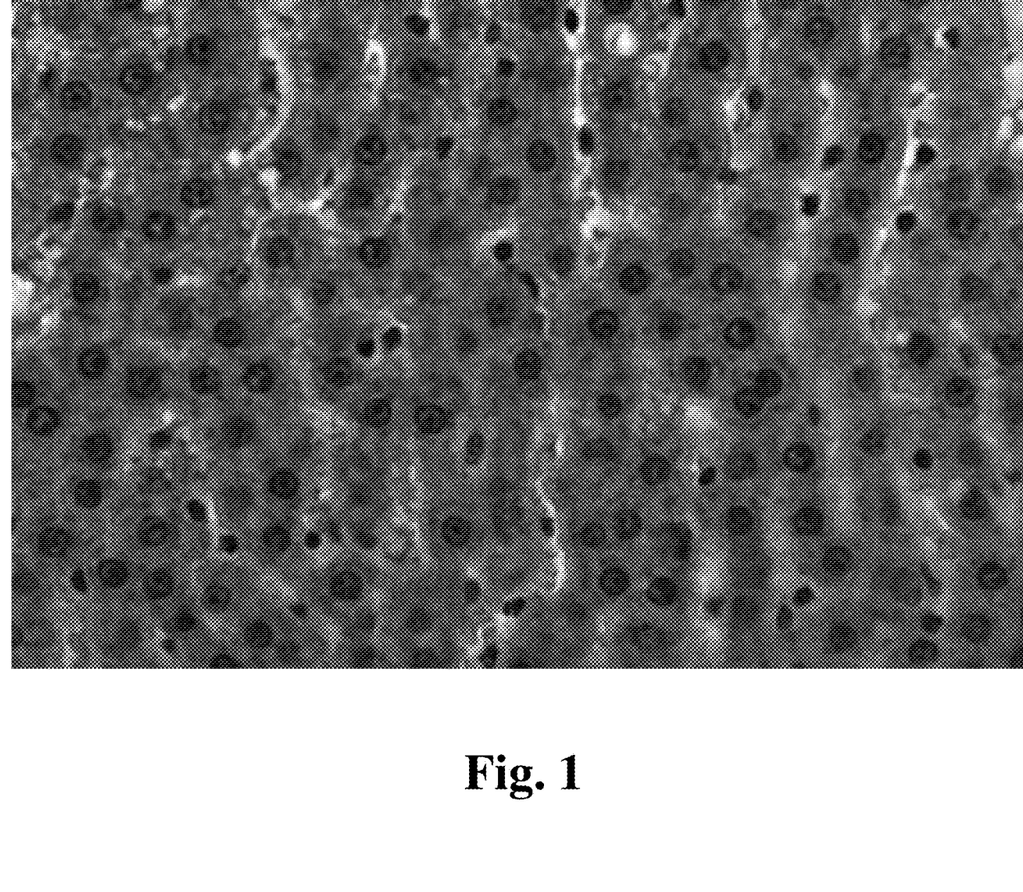
FIG. 1. The morphology of liver tissue from rats fed with normal diet (Group A).
Figure 2:
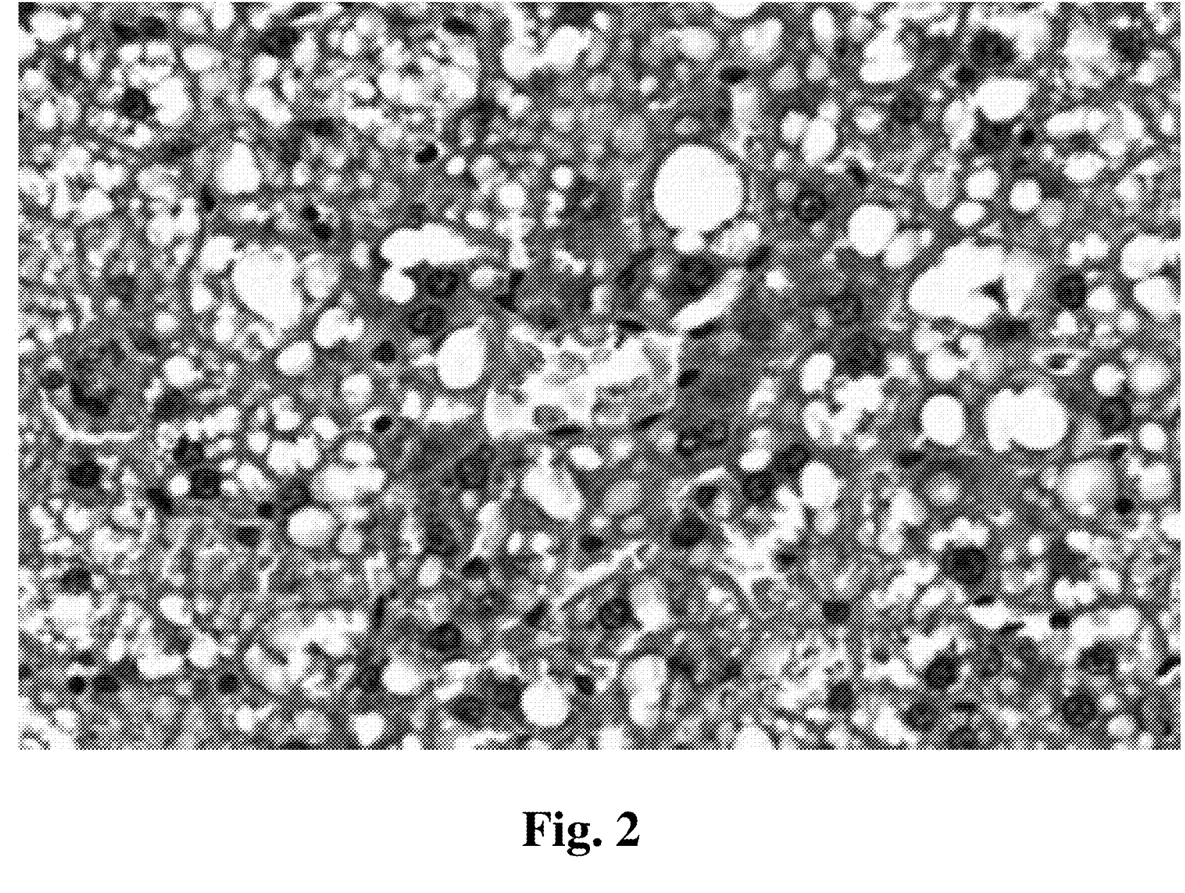
FIG. 2. The morphology of liver tissue from rats fed with high lard diet (Group B).
Figure 3:
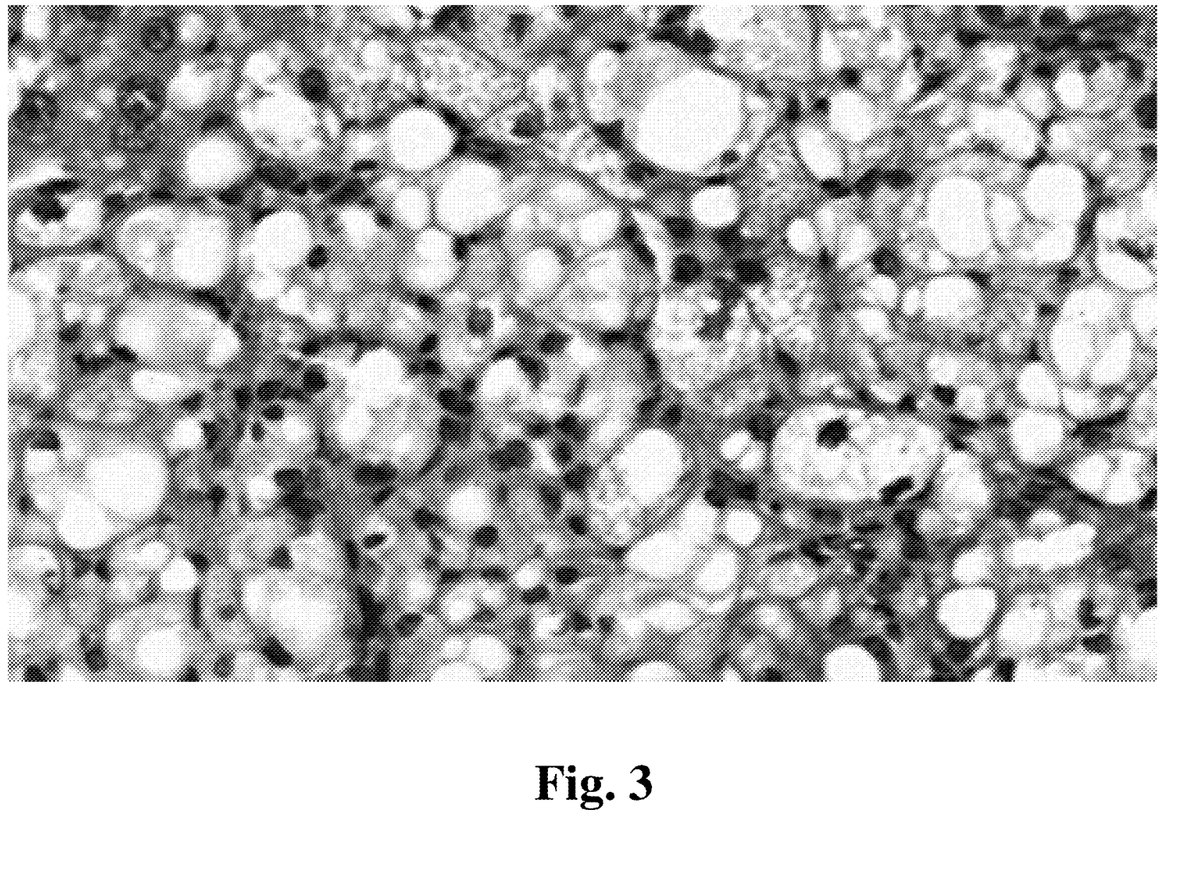
FIG. 3. The morphology of liver tissue from rats fed with refined rapeseed oil diet (Group C).
Figure 4:
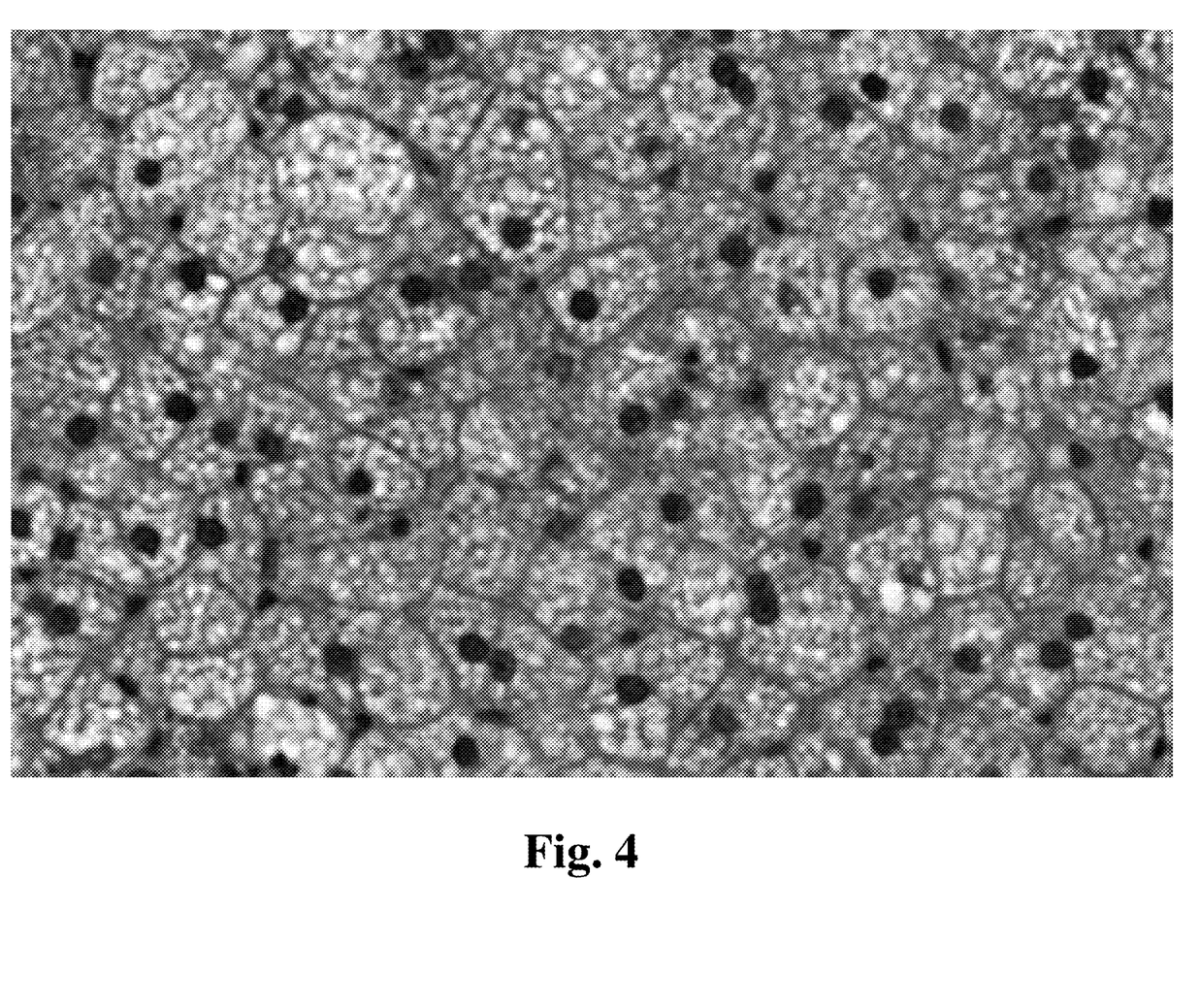
FIG. 4. The morphology of liver tissue from rats fed with cold-pressed rapeseed oil diet (Group D).
Figure 5:
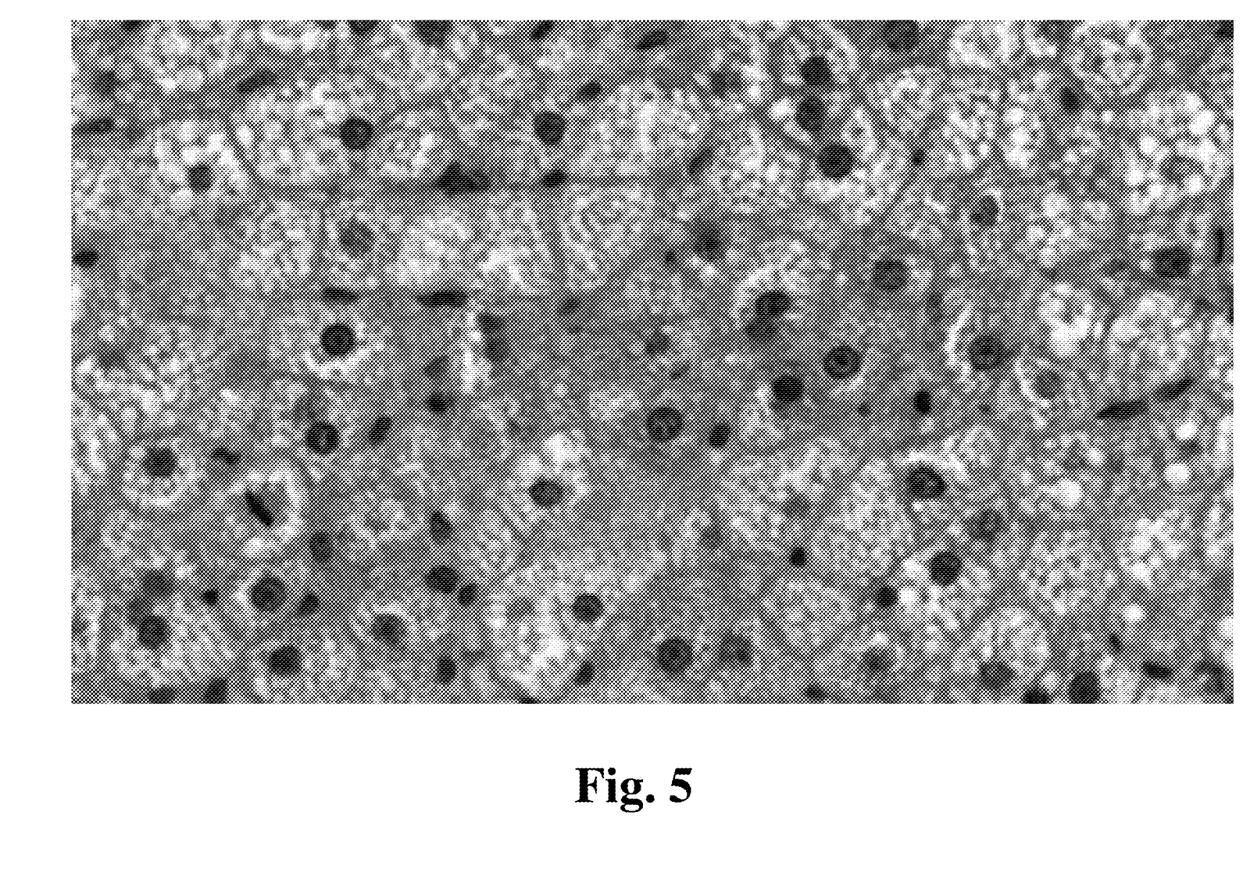
FIG. 5. The morphology of liver tissue from rats fed with hot-pressed rapeseed oil diet (Group E).
Figure 6:
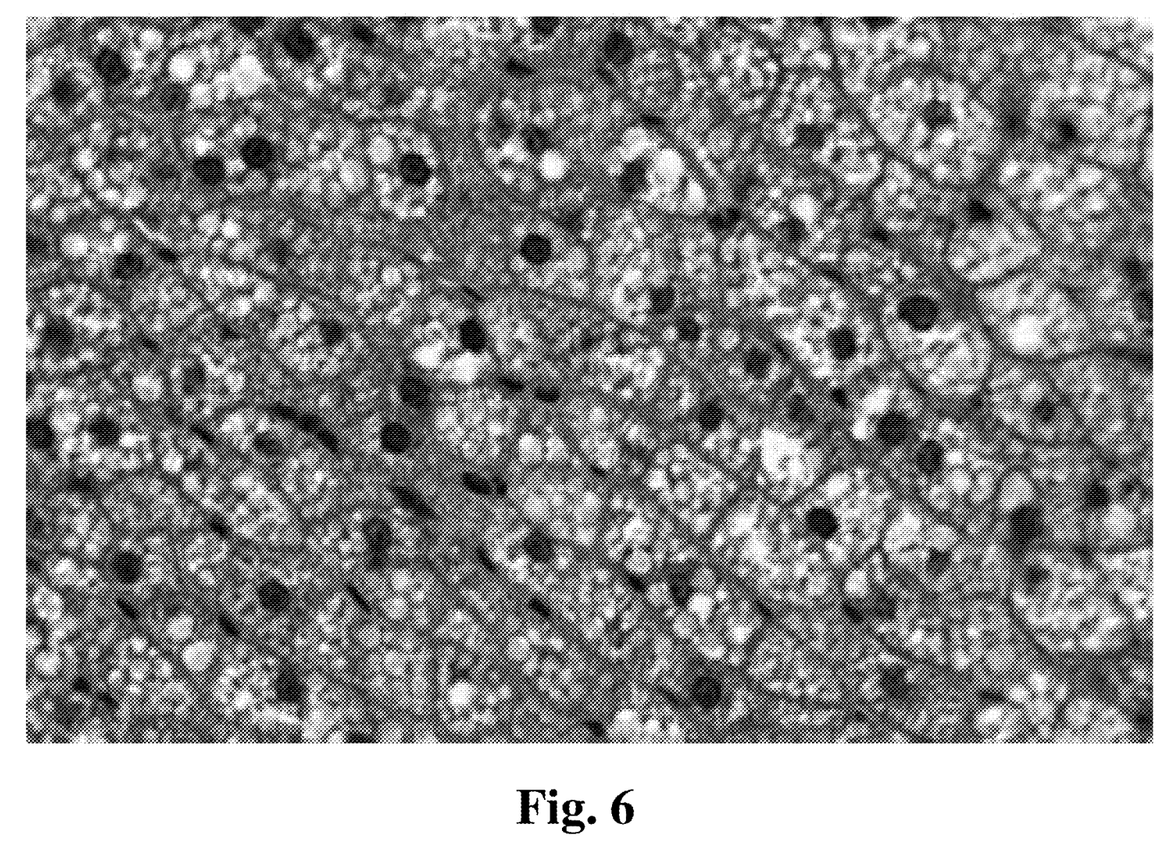
FIG. 6. The morphology of liver tissue from rats fed with rapeseed oil of the present invention (Group F).
Figure 7:
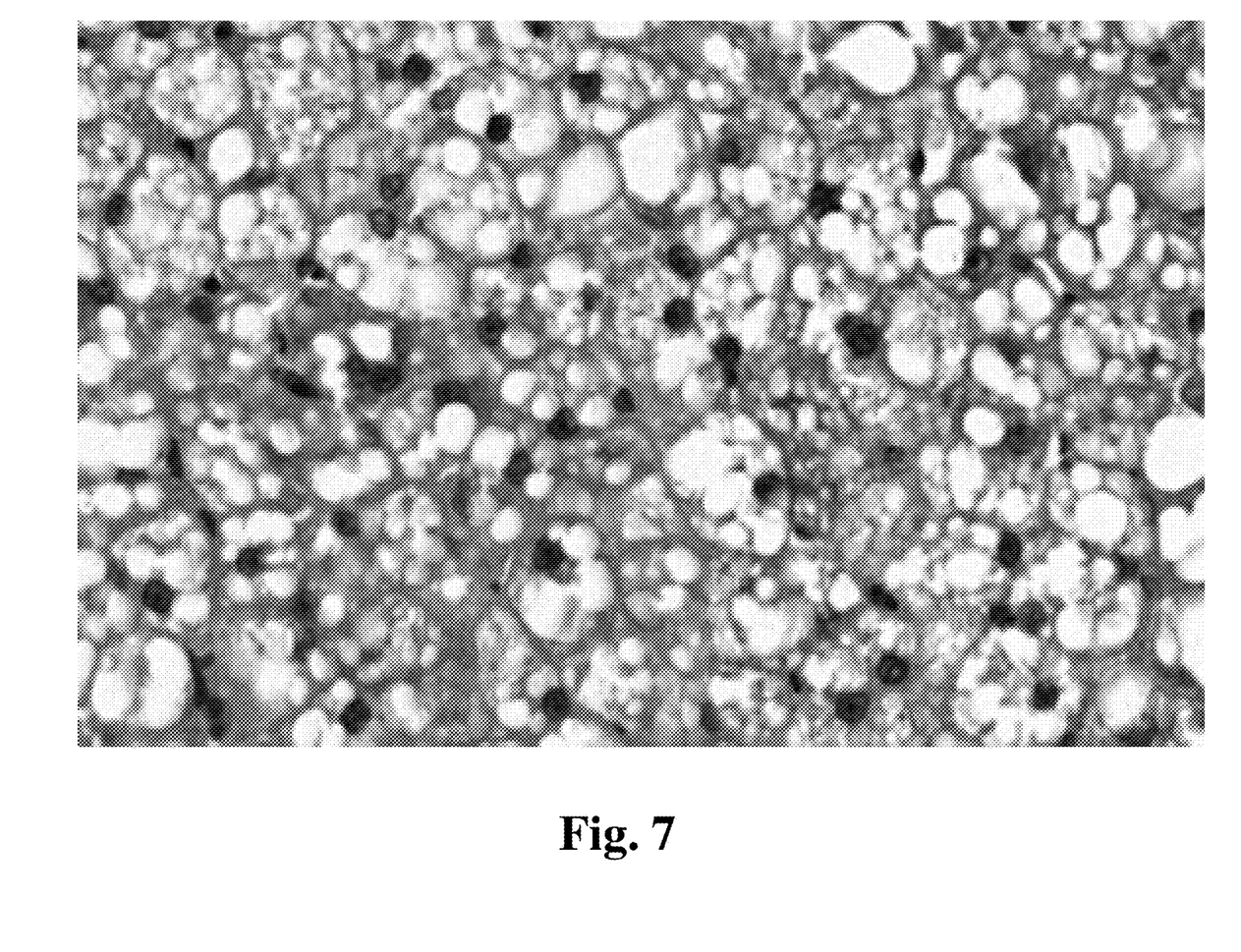
FIG. 7. The morphology of liver tissue from rats fed with extracted rapeseed oil (Group G).

(3) Effects of Feeding Hyperlipidemia Rats with Rapeseed Oils on their Liver Cell Histopathology Microscopic images of liver cell histopathology in rats with different feeds are shown in FIGS. 1-7. It can be seen that the liver cells of rats with a normal diet (FIG. 1) are arranged in a radial order, and the cytoplasm is rich with clear boundaries. Among all the high fat diet groups, liver cells of rats fed with rapeseed oil of the invention (FIG. 6) are most similar to those of the normal rats in terms of the morphology, ie, the hepatocytes maintain a radially complete cell arrangement and structure. Lipid vacuoles of different sizes were found in the cytoplasm of liver cells in rats with a high fat lard diet (FIG. 2). In the rats fed with refined rapeseed oil (FIG. 3) and n-hexane extracted rapeseed oil (FIG. 7), the intracellular fat droplets in the liver cells were larger and the intercellular gaps were not clear. The intracellular fat droplets in the liver cells of rats fed with rapeseed oil made of the cold pressed (FIG. 4), the hot pressed (FIG. 5), and the aqueous enzymatic method (FIG. 6) were relatively smaller.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for producing rapeseed oil by a semi-solid aqueous enzymatic process, comprising the steps of:
    1) cleaning rapeseeds to remove debris, shriveled seeds, and impurities;
    2) adjusting moisture content of the rapeseeds to 8-10 wt %;
    3) pressing the rapeseeds obtained in step 2) to obtain rapeseed embryo flakes which are treated at 50° C.-70° C. to adjust the moisture content to be 3.5-4.5 wt %, and thus obtaining mature rapeseed flakes;
    4) crushing the mature rapeseed flakes and sieving the crushed rapeseeds to obtain an oil-producing powder;
    5) mixing the oil-producing powder and water at a mass ratio of 1:1 to make a semi-solid rapeseed paste;
    6) adding 0.5% to 2% (w/w) of total enzyme (pectinase: cellulase:alkaline protease=1:1:1, by weight) to the semi-solid rapeseed paste, and stirring and mixing at 40-60° C. for 1-2 hr;
    7) centrifuging the rapeseed paste of step 6) to separate crude oil from solid residues;
    8) adding water to the crude oil at 0.2-0.4 L/kg oil, and centrifuging the oil-water mixture at 40-60° C. to obtain a clear rapeseed oil; and
    9) drying the clear rapeseed oil under vacuum to obtain final rapeseed oil product.

2. The method of claim 1, wherein, in the step 6), the mixing temperature is under gradient control by the following steps: keeping the temperature at 40° C. for 20-40 min, raising it to 60° C. within 20-40 min, and maintaining it at 60° C. for 20-40 min.

3. The method of claim 1, wherein the mature rapeseed flakes were sieved through 40~80 mesh sieve in step 4).

4. The method of claim 1, wherein the stirring speed in step 6) is 10~20 rpm.

5. The method of claim 1, wherein, in step 7), the centrifugation speed used to separate the crude oil and the solid residues is 3500 rpm.

6. The method of claim 1, wherein, in step 8), the centrifugation speed used to separate the clear oil from water is 6500 rpm.

7. The method of claim 1, wherein the mature rapeseed flakes were sieved through a 40~80 mesh sieve in step 4); wherein the stirring speed in step 6) is 10~20 rpm and the centrifugation speed used to separate the crude oil and the solid residues is 3500 rpm in step (7); and wherein the centrifugation speed used to separate the clear oil from water is 6500 rpm in step 8).

* * * * *